(12) United States Patent
Mühlbauer et al.

(10) Patent No.: US 6,530,685 B1
(45) Date of Patent: *Mar. 11, 2003

(54) ARRANGEMENT FOR MIXING MULTI-COMPONENT COMPOSITIONS IN PARTICULAR FOR DENTAL PURPOSES

(75) Inventors: Wolfgang Mühlbauer, Hamburg (DE); Hans Hörth, Hamburg (DE)

(73) Assignee: Ernst Muhlbauer KG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/439,027

(22) Filed: Nov. 12, 1999

(30) Foreign Application Priority Data

Nov. 20, 1998 (DE) .......................... 298 20 832

(51) Int. Cl.⁷ .................................. B01F 5/06
(52) U.S. Cl. .................. 366/336; 222/145.6
(58) Field of Search ................. 366/336, 339, 366/340, 181.5; 222/135–137, 145.5, 145.6, 459; 433/90

(56) References Cited

U.S. PATENT DOCUMENTS

| | | | |
|---|---|---|---|
| 4,538,920 A | * | 9/1985 | Drake |
| 4,690,306 A | * | 9/1987 | Staheli |
| 4,753,536 A | * | 6/1988 | Spehar et al. |
| 4,969,747 A | * | 11/1990 | Colin et al. |

* cited by examiner

*Primary Examiner*—Charles E. Cooley
*Assistant Examiner*—David L. Sorkin
(74) *Attorney, Agent, or Firm*—Alix, Yale & Ristas, LLP

(57) ABSTRACT

Arrangement for mixing multi-component compositions, in particular for dental purposes, comprising a component-extruding device with outlet openings (16, 17) assigned to the components and a mixer (11), the inlet openings of which can be connected to the outlet openings (16, 17) of the extruding device. The inlet and outlet openings of these two parts are enclosed by complementary guiding surfaces of the two parts. They open out diametrically in mutually opposite surface portions of the guiding surfaces. As a result, the compressive forces acting in the region of the inlet and outlet openings on both sides cancel one another out, so that a sealed connection can be ensured even without great structural expenditure.

10 Claims, 1 Drawing Sheet

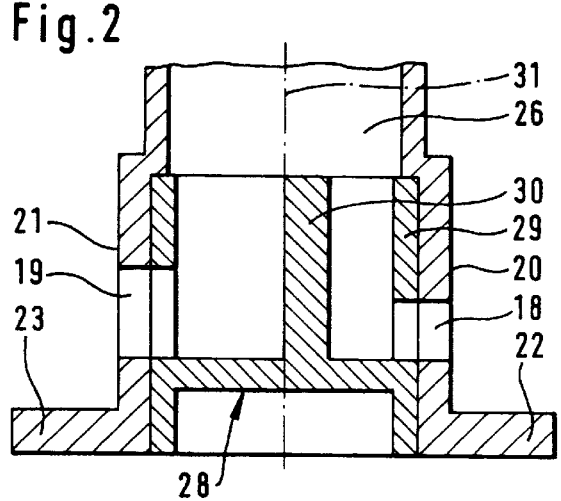
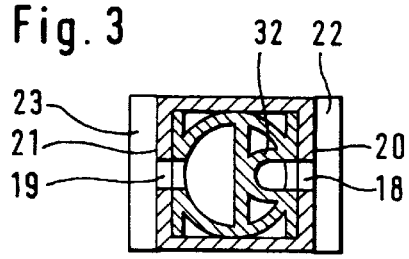
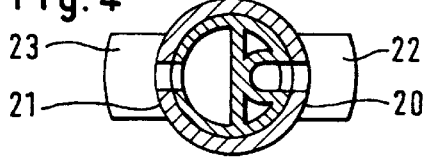
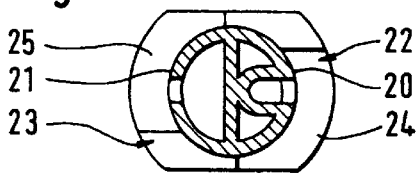
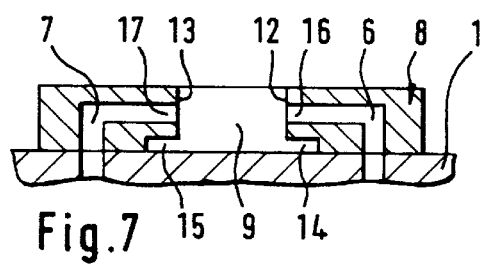
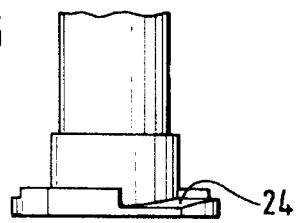
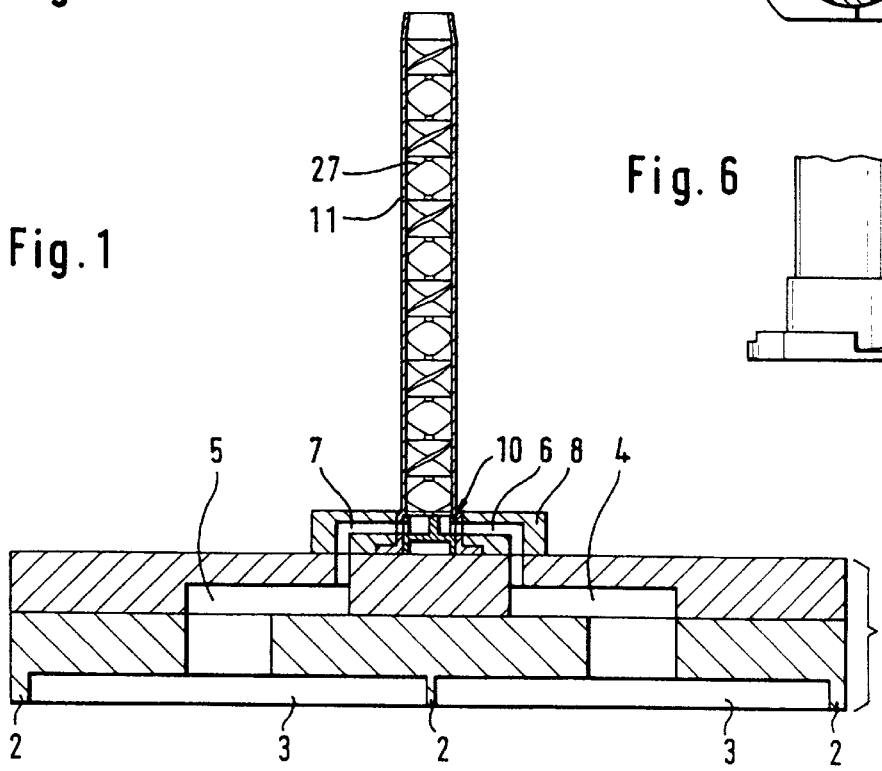

ARRANGEMENT FOR MIXING MULTI-COMPONENT COMPOSITIONS IN PARTICULAR FOR DENTAL PURPOSES

FIELD OF THE INVENTION

The invention relates to an arrangement for mixing multi-component compositions, in particular dental impression compositions, which comprises a component-extruding device and a mixer. The inlet openings of a mixer can be connected to the outlet openings of the extruding device assigned to the components. For example, the inlet openings of the said mixer may be designed in the form of pipe spigots which are cylindrical or slightly conical on the outside and can be inserted in a sealing manner into the outlet openings of the extruding device. The outer surfaces of the pipe spigots and the inner surfaces of the outlet openings interact as guiding surfaces for the connection. The guiding surfaces of one part are designed to complement the guiding surfaces of the other part.

BACKGROUND OF THE INVENTION

The extruding pressure, which has a tendency to lift the mixer off the extruding device, acts in the region of the openings. Therefore, a device which presses the mixer against the extruding device counter to this force must be provided. In order that the sealed connection is ensured, this pressing device must permanently ensure adequate force and accuracy (EP-B-492 412). It is known (DE 3237353 A1) to arrange the openings in such a way that they penetrate the guiding surfaces transversely. The openings are offset axially with respect to one another in order to prevent the two components from coming into contact in the inlet region and hardening there. In this arrangement, the compressive forces acting in the openings only partially cancel one another out.

SUMMARY OF THE INVENTION

According to the invention, the openings open out in a diametrical arrangement in mutually opposite surface portions of the guiding surfaces. The compressive forces acting in the openings thereby largely cancel one another out. The holding devices, which are provided for securing the connecting position of the openings, are subjected only to the load of that force which corresponds to the pressure drop in the mixer. Also provided within the inlet region of the mixer is a wall, the extent of which is large enough that the limit of the region in which the hardening of the composition is to be expected is sufficiently far away from the outlet openings and inlet openings.

If a dynamic mixer is concerned, this wall is expediently arranged at that end plate of the mixer which forms the bearing opening for the mixer shaft. If a static mixer is concerned, an insert which is inserted into the relevant end of the mixer housing and on which this wall is arranged may be provided.

The arrangement is expediently symmetrical with respect to the centre axis of the mixer. The openings open out laterally, transversely with respect to this axis.

In the case of a particularly advantageous embodiment of the invention, the guiding surfaces arranged on the one hand on the extruding device and on the other hand on the mixer define a pushing-in direction running transversely with respect to the center axis of the mixer and transversely with respect to the opening orifices. Transversely with respect to this pushing-in direction (i.e. in the direction of the mixer center axis), they are positively connected to one another.

In the case of another embodiment of the invention, the guiding surfaces are essentially cylindrical and can be locked in the connected position by a bayonet fixing or the like.

A BRIEF DESCRIPTION OF THE DRAWING

The invention is explained in more detail below with reference to the drawing, which illustrates advantageous exemplary embodiments and in which:

FIG. 1 shows a longitudinal section through the end plate of the extruding device with the mixer connected, FIG. 2 shows an enlarged longitudinal section through the base region of the mixer, FIGS. 3–5 show cross sections through the base region of various embodiments of the mixer, FIG. 6 shows a side view of the base region of the embodiment according to FIG. 5, and FIG. 7 shows a longitudinal section through the die ring of the extruding device.

DETAILED DESCRIPTION OF A PREFERRED EMBODIMENT

The end plate 1 of the extruding device has rims 2 which are arranged on the rear in circular form and enclose securing depressions 3 for the front ends of two cartridges. The outlet openings of the cartridges can be connected to two channels 4, 5 in the end plate 1, which open out such that they are directed diametrically towards one another into outlet channels 6, 7 of a plate-shaped die ring 8. In the centre of the die ring 8 there is a recess 9 for receiving the base 10 of a mixing die 11. For this purpose, the recess 9 is bounded by guiding surfaces 12, 13, the distance between which is exactly adapted to the width of the mixer base and which are provided with undercuts 14, 15.

In the guiding surfaces 12, 13, the orifices 16, 17 of the channels 6, 7 lie exactly at that point at which the inlet openings 18, 19 of a mixer base 10 are located when the said mixer base is fitted. These openings open in side surfaces 20, 21, the form and dimensions of which correspond exactly to those of the guiding surfaces 12, 13 of the die ring 8 and interact with the latter as guiding surfaces on the mixer side. The guiding surfaces 12, 13 and 20, 21 surround the associated openings 16, 17 and 18, 19, respectively, and seal these openings off with respect to the outside by their contact against one another in the fitted state of the mixer.

The seating of the mixer base 10 in the recess 9 of the die ring 8 is secured by flanks 22, 23, which project laterally from the mixer base, engaging in a fitting manner into the undercuts 14, 15 of the recess 9. The flanks 22, 23 and the undercuts 14, 15, formed to complement them, may assume various shapes. FIGS. 3 to 6 illustrate three exemplary embodiments. In the exemplary embodiment according to FIG. 3, it is presupposed that the mixer flanks project on both sides of a cross-sectionally square mixer base. In a corresponding way, the guiding surfaces 12, 13 of the recess 9 are formed such that they are planar and parallel with respect to one another. The recess 9 is open in the direction transverse to the plane of the drawing (towards the viewer of FIG. 7), so that the mixer base can be pushed into the recess 9 parallel to the end plate 1 (from the viewer). The pushing-in direction runs transversely with respect to the plane of the drawing or with respect to the centre axis 31. The recess 9 is provided with a stop surface, which determines the pushing-in end position of the mixer base and is arranged in such a way that, in this end position, the outlet openings 16, 17 are exactly in line with the inlet openings 18, 19 of the mixer.

The exemplary embodiments of FIGS. 4 to 6 presuppose that the mixer base 10 (apart from the flanks 22, 23) is of a cylindrical design. In a corresponding way, the guiding surfaces 12, 13 of the recess 9 are designed as parts of a matching, cylindrical surface of a bore. This is cut out at two opposite points, which are offset by 90° with respect to the outlet openings 16, 17, for the passing through of the flanks 22, 23. Once the mixer base has been fitted into the recess 9, it is turned through 90° until the flanks 22, 23 lie in the undercuts 14, 15 and the outlet openings 16, 17 are in line with the inlet openings 18, 19 of the mixer base. The flanks 22, 23 in this case form a bayonet fixing with the corresponding parts of the die ring 8.

This also applies to the exemplary embodiment according to FIGS. 5 and 6. This differs from that according to FIG. 4 in that the flanks 22, 23 are somewhat wider and have obliquely running wedge surfaces 24, 25, to which complementary wedge surfaces in the undercuts 14, 15 correspond. When the mixer base is turned through 90° into that position in which the outlet openings and inlet openings 16 to 19 are in line with one another, these wedge surfaces effect an additional fixing of the mixer base in the axial direction.

In all the examples, the outlet openings 16, 17 and the inlet openings 18, 19 lie symmetrically with respect to the centre axis 31 of the die ring 8 and of the mixer 11.

The mixer interior space 26, which may contain known mixing chicanes 27, is closed with respect to the rear by a plug 28, the side wall 29 of which is adapted exactly to the form of the interior space of the mixer base and is fixed therein in a suitable way, for example, by adhesive bonding. The side walls 29 are crossed through by the inlet openings 18, 19. Between these openings, the plug 28 forms a separating wall 30, which ensures that the flows of the components penetrating through the inlet openings 18, 19 into the mixer cannot meet one another in the direct vicinity of the inlet openings 18, 19 but only at a certain distance from them. This ensures that the composition located at these openings is still flowable even after a normal time difference between discharging successive batches. This is a precondition for the mixer to be changed and for the components flowing into a new mixer once it has been fitted to be of the required consistency. As best seen in FIG. 2, the wall 30 extends in blocking relationship to flow of any component into either inlet opening 18, 19. The wall 30 together with the other structure of the mixer directs flow from the inlet opening 18 and inlet opening 19 in an upward (as viewed) direction. As shown in FIG. 2, the wall 30 extends beyond any part of the inlet opening 18 and any part of the inlet opening 19 in a first or upward direction a distance that is approximately equal to the maximum cross-sectional dimension of the inlet openings 18, 19.

A second wall 32 may confine the inlet spacer of the mixer which is assigned to the inlet opening 18 in the examples represented more narrowly than the inlet space assigned to the other inlet opening 19. As a result, not only is an additional separation of the run-in regions created, but the inlet resistance of the mixer can also be varied to match different viscosities of the components in such a way that the extruding force for the components is approximately the same in spite of the differing viscosity.

In order that the mixer cannot be fitted on the wrong way round in the case of differently shaped outlet or inlet openings (as for example in the embodiments represented), the mutually complementary guiding surfaces 12, 13 and 20, 21 or the flanks 22, 23 and the associated passages or undercuts 14, 15 may be of an unsymmetrical design.

What is claimed is:

1. A dental apparatus for mixing associated multi-component compositions having first and second components which comprises:

a component-extruding device, said component-extruding device including passage means for delivering the first and second components respectively in first and second discrete physically isolated passages, said first and second discrete physically isolated passages in said component-extruding device having respective first and second outlet openings, said component-extruding device having a first guiding surface thereon, said first and second outlet openings communicating with said first guiding surface, said component-extruding device defining a central recess with cut out portions; and a mixer, said mixer including mixer passage means for receiving the first and second components respectively in third and fourth discrete physically isolated passages, said third and fourth discrete physically isolated passages having respective first and second inlet openings, said mixer having a second guiding surface thereon, said first and second inlet openings communicating with said second guiding surface, said first guiding surface on said component-extruding device and said second guiding surface on said mixer being dimensioned and configured to register said first outlet in sealing engagement with said first inlet and said second outlet in sealing engagement with said second inlet upon being received by said component-extruding device with said first inlet opening and first outlet opening extending generally radially in a first direction and said second inlet opening and second outlet opening extending generally radially in a second direction from opposite surface portions of said guiding surfaces, said mixer including a wall separating said first and second inlet openings, said mixer comprising opposed flanks which are received in said cut out portions to connect said mixer to said component-extruding device.

2. The apparatus in accordance with claim 1, wherein the wall is part of an insert that is dimensioned and configured to be inserted into said mixer.

3. The apparatus in accordance with claim 2, wherein said surface portions have a center axis and said mixer has a center axis, said center axis of said surface portions coinciding with said center axis of said mixer.

4. The apparatus in accordance with claim 3, wherein the mixer has a center axis, the guiding surface of the mixer has a pushing-in direction that is parallel to said center axis of said mixer and said mixer is positively connected to said component-extruding device in the direction of said center axis of said mixer.

5. The apparatus in accordance with claim 4, wherein the guiding surfaces are substantially cylindrical, said apparatus including bayonet locking means for locking said component-extruding device and said mixer together.

6. The apparatus in accordance with claim 2, wherein the mixer has a center axis, the guiding surface of the mixer has a pushing-in direction that is transverse to said center axis of said mixer and said mixer is positively connected to said component-extruding device in the direction of said center axis of said mixer.

7. The apparatus in accordance with claim 1, wherein said surface portions have a center axis and said mixer has a center axis, said center axis of said surface portions coinciding with said center axis of said mixer.

8. The apparatus in accordance with claim 7, wherein the guiding surfaces are substantially cylindrical, said apparatus including bayonet-locking means for locking said component-extruding device and said mixer together.

9. The apparatus in accordance with claim 1, wherein the mixer has a center axis, the guiding surface of the mixer has a pushing-in direction that is transverse to said center axis of said mixer and said mixer is positively connected to said component-extruding device in the direction of said center axis of said mixer.

10. The apparatus in accordance with claim 1, wherein the guiding surfaces are substantially cylindrical, said apparatus including bayonet-locking means for locking said component-extruding device and said mixer together.

* * * * *